United States Patent
Kim (10) Patent No.: US 10,281,460 B2
(45) Date of Patent: May 7, 2019

(54) POLYPORUS SQUAMOSUS-DERIVED RECOMBINANT LECTIN SPECIFIC FOR SIALIC ACID LINKAGE

(71) Applicant: Korea Research Institute of Bioscience and Biotechnology, Daejeon (KR)

(72) Inventor: Seonghun Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 104 days.

(21) Appl. No.: 15/037,637

(22) PCT Filed: Nov. 14, 2014

(86) PCT No.: PCT/KR2014/010973
§ 371 (c)(1),
(2) Date: May 18, 2016

(87) PCT Pub. No.: WO2015/072785
PCT Pub. Date: May 21, 2015

(65) Prior Publication Data
US 2016/0290997 A1    Oct. 6, 2016

(30) Foreign Application Priority Data
Nov. 18, 2013   (KR) .................. 10-2013-0140154

(51) Int. Cl.
*C07K 14/375* (2006.01)
*G01N 33/53* (2006.01)
*G01N 33/569* (2006.01)

(52) U.S. Cl.
CPC ....... *G01N 33/5308* (2013.01); *C07K 14/375* (2013.01); *G01N 33/56911* (2013.01); *G01N 33/56983* (2013.01); *G01N 2400/00* (2013.01); *G01N 2469/10* (2013.01)

(58) Field of Classification Search
None
See application file for complete search history.

(56) References Cited

U.S. PATENT DOCUMENTS

| 5,330,897 A | 7/1994 | Pindak et al. |
| 2010/0292453 A1 | 11/2010 | Segal et al. |

FOREIGN PATENT DOCUMENTS

| KR | 10-1054672 | 8/2011 |
| WO | 1993/18782 | 9/1993 |
| WO | WO1999057150 | 11/1999 |
| WO | WO2006091942 | 8/2006 |

OTHER PUBLICATIONS

Ito et al. (Journal of Biomolecular NMR vol. 28, pp. 357-404).*
Mo et al. (Apr. 7, 2000) "Purification and Characterization of a Neu5Acα2-6Galβ1-4Glc/ GlcNAc-specific Lectin from the Fruiting Body of the Polypore Mushroom Polyporus squamosus," Journal of Biological Chemistry, 275(14):10623-10629.
Burgess (Jan. 1, 2009) "Refolding Solubilized Inclusion Body Proteins," Methods in Enzymology. 463:259-282.
Supplementary European Search Report corresponding to European Patent Application No. EP14861999, dated Aug. 11, 2016.
Tateno et al. (2004) "Cloning, Expression in *Escherichia coli* and Characterization of the Recombinant Neu5Acα2,6Galβ1,4GlcNAc-Specific High-Affinity Lectin and its Mutants from the Mushroom *Polyporus squamosus*," Biochem. J. 382:667-675.
International Search Report for corresponding international application PCT/KR2014/010973, dated Feb. 25, 2015.

* cited by examiner

*Primary Examiner* — Robert A Zeman
(74) *Attorney, Agent, or Firm* — Leydig, Voit & Mayer, Ltd.

(57) ABSTRACT

The present invention relates to a method for producing a *Polyporus squamosus*-derived PSL1b recombinant lectin, which binds specifically to sialic acid containing glycoconjugates, from an *Escherichia coli* PSL1b strain (deposit number: KCTC12507BP) or a *Pichia pastoris* PSL1b strain (deposit number: KCTC12500BP) and a lectin produced thereby. The recombinant lectin of the present invention can be useful as an active ingredient of a composition or a kit for measuring or detecting glycoproteins, glycopeptides, glycolipids, sugar precursors, or oligosaccharides having sialic acid moieties.

5 Claims, 5 Drawing Sheets
Specification includes a Sequence Listing.

POLYPORUS SQUAMOSUS-DERIVED RECOMBINANT LECTIN SPECIFIC FOR SIALIC ACID LINKAGE

CROSS-REFERENCE TO RELATED APPLICATIONS

This application is a U.S. National Stage Application filed under 35 U.S.C. § 371 of International Application No. PCT/KR2014/010973, filed Nov. 14, 2014, which claims the benefit of Korean Application No. 10-2013-0140154, filed Nov. 18, 2013. Both of these applications are hereby incorporated by reference in their entireties.

BACKGROUND OF THE INVENTION

1. Field of the Invention

The present invention relates to a gene encoding a lectin specifically binding to sialoglycoconjugates, which is originated from the mushroom *Polyporus squamosus*, an active lectin protein obtained by expressing the said gene in a heterologous host, a recombinant transformant producing the said protein, and a method for measuring the biological material including glycoproteins, glycopeptides, glycolipids, sugar precursors, or oligosaccharides containing sialic acid moieties.

2. Description of the Related Art

Sialic acid (Neuraminic acid; Neu5Ac) is the alpha-ketoaldonic acid containing 9 carbons, which is a sugar found in the non-reduced end of a glycoconjugate such as glycoprotein, glycolipid, and oligosaccharide. Again, sialic acid is a sugar existing at the end of a glycoconjugate. Up to date, approximately 80 kinds of glycoconjugates bound with sialic acid have been identified in the natural world. Sialic acid plays an important role in biological phenomenon in cells, for example cell/cell interaction, functioning as a precursor determining the intracellular signal, and stabilization of a glycoprotein, etc. In particular, endogenous sialic acid is known as one of the glycans that is recognized first after the infection of a pathogen (Sasisekharan and Myette, 2003, *Am. Sci.* 91, 432; Vimr and Lichtensteiger, 2002, *Trends Microbiol.* 10, 254). Sialic acid on the cell surface is also known as a component forming a poly-oligosaccharide in the form of a capsule for cell protection or involved in immune privilege even in the pathogen itself (Vimr et al., 2004, *Microbiol. Mol. Biol. Rev.* 68, 132). The chemical structure of sialic acid is very complicated, which is composed of the carboxyl group connected to anomeric site of the second carbon and the glycerol structure found in deoxy of the third carbon and the sixth carbon. In the sialoglycoconjugate structure, the sialic acid is linked to other sugars via alpha(2,3)-, alpha(2,6)-, alpha(2,8)-, and alpha(2,9)-linkage. In addition the hydroxyl residue of sialic acid sugar is substituted with O-acetyl, O-phosphate, O-sulfate, O-methyl, and N-glycosyl group, resulting in producing a more complicated chemical structure such as transformants with N-glycolylneuraminic acid (NeuGc). Because of such a complicated chemical structure, it is very difficult to measure glycoconjugates containing sialic acid accurately. Due to the advanced new analysis techniques based on mass spectrometer and nuclear magnetic resonance spectrometer, etc, the analysis of a glycan structure containing sialic acid is more accurately achieved than before. However, there is still a problem to solve such as the lack of the amount of a biological sample and the complexity in the preparation of a sample for the analysis (Cohen and Varki, 2010, *OMICS* 14, 455; Alley et al. 2013, *Chem. Rev.* 113, 2668).

To measure the complicated structure of a sialic acid conjugated glycans, lectins have been applied to detect glycan structures (Vanderschaeghe et al., 2010, *Biol. Chem.* 391, 149; Hsu and Mahal, 2009, *Curr. Opin. Chem. Biol.* 13, 427). Lectins are multivalent carbohydrate binding proteins that display neither catalytic activity nor antibody like characteristics. Lectin, found in a wide range of living things from microorganisms to higher animals, is one of the proteins that can bind to sugar chains, which is involved in various life phenomena including protein quality control, host-pathogen interaction, cell-cell communication, inflammation, immune response, cancer progression, and development, by binding specifically to glycans (Lam and Ng, 2011. *Appl. Microbiol. Biotechnol.* 89, 45). Lectin was first isolated from *Ricinus communis* by the Russian scientist Sillmark in the late $19^{th}$ century. Since then, 40 kinds of lectins including Concanavlain A (ConA) have been identified, studied, and used in various fields. Those lectins identified so far are extracted and purified from various natural bioresources, which are used to detect sialic acid (Neu5Ac, Neuraminic acid), galactose (Gal), N-acetylglucosamine (N-GlcNAc), fucose (Fuc), mannose (Man), and glucose (Glc) (Lehmann et al., 2006, *Cell. Mol. Life Sci.* 63, 1331; Singh et al., 2010 *Crit. Rev. Biotechnol.* 30, 99; Kajiwara et al., 2010, *Microbes Environ.* 25, 152).

However, due to the variety of structures of glycoconjugates having alpha and beta linkages and the variety of possible monomer combinations in glycoconjugates or side-chain modifications, hundreds or thousands of different glycan structures are possible theoretically. However the limited number of identified lectins are available for detection of a variety of glycan structures. In particular, *Maackia amurensis* (MAA), *Sambucus nigra* (SNA), and *Limulus polyphemus* lectin can be used for detection of sialic acid (Neu5Ac) containing glycan structures but the lectin could not accurately distinguish α2,3-, α2,6-, and α2,8-linkages, the chemical specificity of sialic acid sugar chain, due to isolectin contamination in the extracted lectin proteins. Besides, the lectin sometimes recognizes specifically Gal and GalNAc binding to sialic acid, leading to non-specific signal because of the non-specific binding. Therefore, it has been requested to develop a novel sialic acid specific lectin with elimination of isolectin interference.

The lectin of the present invention was isolated and purified from *Polyporus squamosus* fruiting body by using β-galactosyl-Synsorb column and DEAE-Sephacel ion exchange column, which was approximately 28 kDa and bound specifically to Neu5Ac-α(2,6)-Gal-β(1,4)-Glc/GlcNAc sugar chain (Mo et al., 2000, *J. Biol. Chem.* 275, 10623). The cDNA sequence obtained from *Polyporus squamosus* by RACE (rapid amplification of cDNA ends) using the degenerated primers constructed based on the partial amino acid sequence of the corresponding lectin was the protein encoding two isolectins PSL1a and PSL1b having 858 bp and 876 bp long sequences respectively. These are presumed to be the proteins in the sizes of 31.04 kDa and 31.998 kDa theoretically (Tateno et al. 2004, *Biochem. J.* 382, 667). The nucleotide sequence encoding PSL1a lectin is expressed in *E. coli* and isolated/purified as an active recombinant protein, whose characteristics have been disclosed. Recently the three-dimensional protein structure of PSL1a lectin was identified as the human-type influenza receptor Neu5Acα(2,6)Galβ(1,4)GlcNAc (Tateno et al. 2004, *Biochem. J.* 382, 667; Kadirvelraj et al., 2011, Glycobiology 21, 973). However, the characteristics of the nucleotide sequence encoding PSL1b lectin cannot be identified yet since it is generated as an inactive protein in *E. coli* (Tateno et al. 2004, *Biochem. J.* 382, 667).

The present inventors tried to obtain *Polyporus squamosus*-derived isolectin PSL1b from a heterologous host as an active recombinant protein that binds specifically to sialic acid. As a result, the inventors chemically synthesized the polynucleotide encoding isolectin PSL1b lectin protein and at last obtained a novel active recombinant lectin protein from the heterologous host system such as *E. coli* and yeast. The present inventors further confirmed that the constructed novel recombinant lectin protein can be used to measure the proteins having different sugar chain structures such as glycoproteins, glycolipids, and oligosaccharides containing sialic acid moieties, to monitor microorganisms, and to explain various life phenomena mediated by glycoconjugates, leading to the completion of the invention.

SUMMARY OF THE INVENTION

It is an object of the present invention to provide a recombinant lectin binding specifically to sialic acid having alpha(2,6)-linkage. To obtain the active recombinant lectin protein from *E. coli* or yeast, the present invention provides a polynucleotide represented by SEQ. ID. NO: 1 encoding the chemically synthesized lectin protein above.

It is another object of the present invention to provide a polypeptide represented by SEQ. ID. NO: 2 transcribed and translated from the polynucleotide above.

It is also an object of the present invention to provide an expression vector containing the polynucleotide above.

It is further an object of the present invention to provide a transformant transfected with the expression vector above.

It is also an object of the present invention to provide a method for preparing the recombinant lectin specifically binding to sialic acid having alpha(2,6)-linkage.

It is also an object of the present invention to provide a method for purifying the recombinant lectin protein from the transformant above.

In addition, the present invention provides a method for using the recombinant lectin for lectin blotting in order to measure the glycoprotein containing sialic acid moieties.

To achieve the above objects, the present invention provides a polynucleotide composed of the nucleotide sequence represented by SEQ. ID. NO: 1 encoding lectin binding specifically to alpha(2,6) sialic acid.

The present invention also provides a polypeptide composed of the amino acid sequence represented by SEQ. ID. NO: 2.

The present invention also provides an expression vector comprising the polynucleotide above.

The present invention also provides a transformant transfected by the expression vector above.

The present invention also provides a bacterial transformant transfected by the expression vector above.

The present invention also provides a method for preparing the recombinant lectin binding specifically to alpha(2,6) sialic acid comprising the following steps:

a) culturing the bacterial transformant above; and
b) separating and purifying the recombinant lectin binding specifically to alpha(2,6) sialic acid from the culture product of step (a).

The present invention also provides a recombinant lectin binding specifically to alpha(2,6) sialic acid prepared by the method above.

The present invention also provides a polynucleotide composed of the nucleotide sequence represented by SEQ. ID. NO: 5.

The present invention also provides a polypeptide composed of the amino acid sequence represented by SEQ. ID. NO: 6.

The present invention also provides a yeast transformant transfected with the expression vector above.

The present invention also provides a method for preparing the recombinant lectin binding specifically to alpha(2,6)sialic acid which comprises the following steps:

(a) culturing the yeast transformant; and
(b) separating and purifying the recombinant lectin binding specifically to alpha(2,6) sialic acid from the culture product of step (a).

The present invention also provides a recombinant lectin binding specifically to alpha(2,6)sialic acid prepared by the method above.

The present invention also provides a polynucleotide composed of the nucleotide sequence represented by SEQ. ID. NO: 9.

The present invention also provides a polypeptide composed of the amino acid sequence represented by SEQ. ID. NO: 10.

The present invention also provides a recombinant *Escherichia coli* strain deposited under the deposit number KCTC12507BP that can produce the recombinant lectin PSL1b protein binding specifically to alpha(2,6)sialic acid containing glycoconjugates.

The present invention also provides a recombinant yeast (*Pichia pastoris*) strain deposited under the deposit number KCTC12500BP that can produce the recombinant lectin PSL1b protein binding specifically to alpha(2,6)sialic acid containing glycoconjugates.

The present invention also provides a method for preparing the recombinant lectin binding specifically to alpha(2,6)sialic acid comprising the following steps:

(a) culturing the strain above; and
(b) separating and purifying the recombinant lectin from the culture product of step (a).

The present invention also provides a recombinant lectin binding specifically to alpha(2,6)sialic acid prepared by the method above.

The present invention also provides a kit for the measurement or quantification of glycoproteins, glycopeptides, glycolipids, sugar precursors, or oligosaccharides having alpha (2,6)sialic acid moieties using the recombinant lectin of the invention.

The present invention also provides a kit for the monitoring, measurement or quantification of the cell lines, bacteria, or viruses having sialic acid sugar chains comprising alpha(2,6)sialic acid on the surface thereof using the recombinant lectin of the invention.

The present invention also provides a method for the measurement or quantification of the sialylated glycoconjugates composed of the glycoproteins, glycopeptides, glycolipids, sugar precursors, or oligosaccharides having sialic acid moieties, which comprises the following steps:

(a) contacting the test sample to the recombinant lectin of the invention; and
(b) analyzing the glycoproteins, glycopeptides, glycolipids, sugar precursors, or oligosaccharides binding to the lectin above.

The present invention also provides a method for the measurement or quantification of the cell lines, bacteria, or viruses having sialic acid moieties, which comprises the following steps:

(a) contacting the test sample to the recombinant lectin of the invention; and (b) analyzing the cells, bacteria, or viruses binding to the lectin above.

The present invention also provides a use of the kit for the measurement or quantification of the glycoproteins, glycopeptides, glycolipids, sugar precursors, or oligosaccharides having alpha(2,6)sialic acid using the recombinant lectin of the invention.

The present invention also provides a use of the kit for the monitoring, measurement or quantification of the cell lines, bacteria, or viruses having sialoglycoconjugates comprising alpha(2,6)sialic acid on the surface thereof using the recombinant lectin of the invention.

Advantageous Effect

The present invention relates to the *Polyporus squamosus*-derived isolectin PSL1b active recombinant lectin protein binding specifically to glycoconjuages containing alpha (2,6) sialic acid moieties. The present invention provides a method for producing the *Polyporus squamosus*-derived PSL1b recombinant lectin, which specifically binds to sialic acid containing glycoconjugates, from an *Escherichia coli* PSL1b strain (deposit number: KCTC12507BP) or a *Pichia pastoris* PSL1b strain (deposit number: KCTC12500BP) and the lectin produced thereby. The recombinant lectin of the present invention can be effectively used for the measurement of glycoproteins, glycopeptides, glycolipids, sugar precursors, or oligosaccharides having sialic acid moieties and as an active ingredient of the composition or the kit for the measurement or detection of the cell lines, bacteria, and viruses having sialoglycoconjugates.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.
The present invention provides a polynucleotide composed of the nucleotide sequence represented by SEQ. ID. NO: 1 encoding lectin binding specifically to alpha(2,6) sialic acid.

The present invention also provides a polypeptide composed of the amino acid sequence represented by SEQ. ID. NO: 2.

The present invention also provides an expression vector comprising the polynucleotide above.

The present invention also provides a transformant transfected by the expression vector above.

The present invention also provides a bacterial transformant transfected by the expression vector above.

The bacteria above are preferably selected from the group consisting of *Staphylococcus aureus*, *E. coli*, *B. cereus*, *Salmonella typimurium*, *Salmonella choleraesuis*, *Yersinia enterocolitica*, and *Listeria monocytogenes*, and among these *E. coli* is more preferred.

In a preferred embodiment of the present invention, the present inventors screened gene sequence candidates by using query sequences provided by National Center for Biotechnology Information (NCBI, accession no. AB120707) in order to produce the *Polyporus squamosus*-derived recombinant lectin protein. Based on the sequences screened by the present inventors, the polynucleotide in 879 bp containing guanine and cytosine 44.7% via codon optimization and RNA secondary structure optimization was chemically synthesized at DNA 2.0 Co (USA) in order to induce the optimum expression of the target gene in the heterologous host system. The polynucleotide sequence synthesized in the present invention and the polypeptide produced from the same by transcription and translation are represented by SEQ. ID. NO: 1 and SEQ. ID. NO: 2 respectively. Changes in the wild type gene encoding the *Polyporus squamosus*-derived lectin PSL1b and the chemically synthesized gene (see Table 1) and codon (see Table 2) were presented. Based on the polynucleotide gene information confirmed before, the primers represented by SEQ. ID. NO: 3 and SEQ. ID. NO: 4 were constructed in order to clone the lectin protein in the *E. coli* expression vector (see Table 3). *Escherichia coli* BL21-CodonPlus(DE3)-RIL was transfected with the recombinant plasmid pET-PSL1b 8× His (see FIG. 1) whose gene sequence had been identified in order to produce the recombinant PSL1b protein therein. The recombinant strain *Escherichia coli* PSL1b expressing the recombinant lectin PSL1b of the invention was deposited at Korean Collection for Type Cultures (KCTC), Korea Research Institute of Bioscience and Biotechnology (KRIBB), on Nov. 1, 2013 (KCTC12507BP). Based on the polynucleotide gene information identified above, the primers represented by SEQ. ID. NO: 7 and SEQ. ID. NO: 8 were constructed in order to clone the lectin protein in the yeast expression vector (see Table 4). *Pichia pastoris* X-33 was transfected with the recombinant plasmid pPICZα-PSL1b 8× His (see FIG. 2) whose gene sequence had been identified in order to produce the recombinant lectin PSL1b therein. The recombinant strain *Pichia pastoris* PSL1b expressing the recombinant lectin PSL1b of the invention was deposited at Korean Collection for Type Cultures (KCTC), Korea Research Institute of Bioscience and Biotechnology (KRIBB), on Oct. 7, 2013 (KCTC12500BP). After culturing the recombinant *E. coli* of the invention, target cells were obtained from the culture medium by centrifugation. To separate the recombinant lectin from the collected cells, HisTrap™ FF column chromatography was performed. As a result, the recombinant lectin was eluted. To purify the recombinant lectin eluted above, Superose 12 column chromatography was performed and as a result, proteins in different sizes were eluted. The eluted proteins were concentrated by using Amicon®Ultra Centrifugal filter 10K. The crude extract for the recombinant lectin purification obtained above proceeded to SDS-PAGE, followed by Coommassie Brilliant Blue staining. The purity and the molecular weight of the purified lectin protein were analyzed by using Precision Plus Protein™ Standards (Bio-Rad, USA) as the standard proteins. As a result, the size of the purified recombinant PSL1b protein separated from *E. coli* was confirmed to be about 32 kDa (see FIG. 3). In addition, in order to purify the recombinant lectin from yeast, the transfected recombinant yeast strain constructed by the method of the invention described above was cultured and the culture solution was collected. To separate yeast cells and the culture medium from the yeast culture solution, centrifugation was performed. The precipitate was eliminated and the supernatant was obtained. To purify the recombinant lectin from the crude enzyme solution above, HisTrap™ FF column chromatography was performed. As a result, the recombinant lectin was eluted. The eluted proteins were concentrated by using Amicon®Ultra Centrifugal filter 10K. The crude protein solution obtained above proceeded to SDS-PAGE, followed by Coommassie Brilliant Blue staining. The purity and the size of the purified lectin protein were analyzed by using Precision Plus Protein™ Standards (Bio-Rad, USA) as the standard proteins. As a result, the size of the recombinant PSL1b protein separated and purified from yeast was about 40 kDa, which was a little larger than that of the protein separated from *E. coli*. The increase of the size was presumed because of the potential 3 N-linked glycosylations containing the corresponding lectin sequence (see FIG. 4). To investigate the selective binding of the protein separated above, lectin blotting was performed. As a result, lectin blot signal was observed in the basic structure of N-linked glycan structure such as Neu5Acα(2,6)Galβ(1,4)GlcNAc and in the fetuin containing O-linked glycan structure such as Neu5Ac α(2,6)Galβ, Neu5Ac α(2,6)Galβ(1,3)GalNA, Neu5Acα(2,6)[Galβ(1,3)]GalNA, Neu5Acα(2,6)Galβ(1,3)[Neu5Acα(2,6)]GalNAc], Neu5Acα(2,6)Galβ(1,3)[Neu5Acα(2,6)Galβ(1,4)GlcNAcβ(1,6)]GalNAc. However, any signal on the lectin-blotting membrane was not observed in the non-sialylated fetuin, the negative control, which contains Galβ(1,4)GlcNAc for N-linked glycan and Galβ, Galβ(1,3)GalNA, [Galβ(1,3)]GalNA, Galβ(1,3)[Galβ(1,4)GlcNAcβ(1,6)]GalNAc for O-linked glycans, and the fetuin containing alpha(2,3) sialic acid (bovine serum fetuin) (see FIG. 5), either.

Therefore, the present invention relates to the active recombinant lectin protein of the *Polyporus squamosus*-derived isolectin PSL1b binding specifically to glycoconjugates containing alpha(2,6)-linked sialic acid moieties. The present invention provides a method for producing the *Polyporus squamosus*-derived PSL1b recombinant lectin, which specifically binds to sialic acid containing glycoconjugates, from an *Escherichia coli* PSL1b strain (deposit number: KCTC12507BP) or a *Pichia pastoris* PSL1b strain (deposit number: KCTC12500BP) and the lectin produced thereby. The recombinant lectin of the present invention can be effectively used for the measurement of glycoproteins, glycopeptides, glycolipids, sugar precursors, or oligosaccharides having sialic acid moieties and as an active ingredient of the composition or the kit for the measurement or detection of the cell lines, bacteria, and viruses having sialoglycoconjugates.

The present invention also provides a method for preparing the recombinant lectin binding specifically to alpha(2,6) sialic acid, comprising the following steps:
(a) culturing the bacterial transformant of the invention; and
(b) separating and purifying the recombinant lectin from the culture product of step (a).

The present invention also provides a method for preparing the recombinant lectin binding specifically to alpha(2,6) sialic acid, comprising the following steps:
(a) culturing the bacterial transformant above; and
(b) separating and purifying the recombinant lectin from the culture product of step (a).

The present invention also provides the recombinant lectin binding specifically to alpha(2,6) sialic acid prepared by the method above.

The present invention also provides a polynucleotide composed of the nucleotide sequence represented by SEQ. ID. NO: 5.

The present invention also provides a polypeptide composed of the amino acid sequence represented by SEQ. ID. NO: 6.

The polypeptide above preferably includes 8 histidine residues at C-terminal of the total amino acid sequence, but not always limited thereto.

The present invention also provides a yeast transformant transfected with the expression vector above.

The yeast herein is preferably selected from the group consisting of *Pichia*, *Saccharomyces*, *Kluyveromyces*, *Yallowia*, *Hansenula*, and *Candida*, and *Pichia* is more preferred.

The present invention also provides a method for preparing the recombinant lectin binding specifically to alpha(2,6) sialic acid, comprising the following steps:
(a) culturing the yeast transformant above; and
(b) separating and purifying the recombinant lectin from the culture product of step (a).

The present invention also provides the recombinant lectin binding specifically to alpha(2,6) sialic acid prepared by the method above.

The present invention also provides a polynucleotide composed of the nucleotide sequence represented by SEQ. ID. NO: 9.

The present invention also provides a polypeptide composed of the amino acid sequence represented by SEQ. ID. NO: 10.

The polypeptide above preferably includes the signal sequence for the secretory expression at N-terminal in the total amino acid sequence, but not always limited thereto.

The present invention also provides a recombinant *Escherichia coli* strain deposited under the deposit number KCTC12507BP that can produce the recombinant lectin PSL1b protein binding specifically to alpha(2,6)sialic acid containing glycoconjugates.

The present invention also provides a recombinant yeast (*Pichia pastoris*) strain deposited under the deposit number KCTC12500BP that can produce the recombinant lectin PSL1b protein binding specifically to alpha(2,6)sialic acid containing glycoconjugates.

The present invention also provides a method for preparing the recombinant lectin binding specifically to alpha(2,6)sialic acid comprising the following steps:
(a) culturing the strain above; and
(b) separating and purifying the recombinant lectin from the culture product of step (a).

The present invention also provides the recombinant lectin binding specifically to alpha(2,6)sialic acid prepared by the method above.

The present invention also provides the lectin binding specifically to the sugar chain structure selected from the group consisting of the followings:

sialylated glycan wherein NeuAc or NeuGc(α2→6) is added to Gal or Glc residue;

sialylated glycan wherein NeuAc or NeuGc(α2→6) is added to Gal(β1→4)Glc or Glc(β1→4)Glc residue;

sialylated glycan wherein NeuAc or NeuGc(α2→6) is added to Gal(β1→4)GlcNAc or Gal(β1→3)GlcNAc residue;

sialylated glycan wherein NeuAc or NeuGc(α2→6) is added to Gal(β1→3)[αFuc(1→4)]GlcNAc residue; and sialylated glycan wherein NeuAc or NeuGc(α2→6) is added to Gal(β1→4)[αFuc(1→3)]GlcNAc.

The present invention also provides a kit for the measurement or quantification of glycoproteins, glycopeptides, glycolipids, sugar precursors, or oligosaccharides having alpha (2,6)sialic acid moieties using the recombinant lectin of the invention.

The present invention also provides the recombinant lectin PSL1b protein binding selectively to alpha(2,6)sialic acid containing glycoconjugates and having the size of 30 kDa~60 kDa, which has been separated and purified by the method of the invention.

The present invention also provides a kit for the monitoring, measurement or quantification of the cell lines, bacteria, or viruses having sialoglycoconjugates comprising alpha(2,6)sialic acid on the surface thereof using the recombinant lectin of the invention.

The present invention also provides a use of the kit for the measurement or quantification of the glycoproteins, glycopeptides, glycolipids, sugar precursors, or oligosaccharides having alpha(2,6)sialic acid containing glycoconjugates using the recombinant lectin of the invention.

The present invention also provides a use of the kit for the monitoring, measurement or quantification of the cell lines, bacteria, or viruses having sialoglycoconjugates comprising alpha(2,6)sialic acid on the surface thereof using the recombinant lectin of the invention.

The present invention also provides a method for the measurement or quantification of the sialylated glycoconjugates composed of the glycoproteins, glycopeptides, glycolipids, sugar precursors, or oligosaccharides having sialic acid moieties, which comprises the following steps:

(a) contacting the test sample to the recombinant lectin of the invention; and (b) analyzing the glycoproteins, glycopeptides, glycolipids, sugar precursors, or oligosaccharides binding to the lectin above.

The present invention also provides a method for the measurement or quantification of the cell lines, bacteria, or viruses having sialic acid sugar chains, which comprises the following steps:

(a) contacting the test sample to the recombinant lectin of the invention; and (b) analyzing the cells, bacteria, or viruses binding to the lectin above.

The *Escherichia coli* PSL1b strain (Deposit No: KCTC12507BP) or *Pichia pastoris* PSL1b strain (Deposit No: KCTC12500BP) of the present invention can produce efficiently the *Polyporus squamosus*-derived PSL1b recombinant lectin binding specifically to sialic acid containing glycoconjugates, so that the strain of the invention can be effectively used as an active ingredient of a composition or a kit for measuring or detecting glycoproteins, glycopeptides, glycolipids, sugar precursors, or oligosaccharides having sialic acid moieties.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Synthesis of Gene for the Production of the *Polyporus squamosus*-Derived Recombinant Lectin Protein To produce the *Polyporus squamosus*-derived recombinant lectin protein, the following experiment was performed.

Particularly, the gene information about the *Polyporus squamosus*-derived lectin was obtained by screening all the similar sequences by using query sequence of National center for Biotechnology Information (NCBI, accession no. AB120707). Based on the sequences screened by the present inventors, the polynucleotide in 879 bp containing guanine and cytosine 44.7% via codon optimization and RNA secondary structure optimization was chemically synthesized at DNA 2.0 Co (USA) in order to induce the optimum expression of the target gene in the heterologous host system. The polynucleotide sequence synthesized in the present invention and the polypeptide produced from the same by transcription and translation are represented by SEQ. ID. NO: 1 and SEQ. ID. NO: 2 respectively. The physical and chemical changes in the wild type gene encoding *Polyporus squamosus*-derived lectin PSL1b and in the chemically synthesized gene are shown in Table 1. The codon changes are presented in Table 2.

TABLE 1

| Content | Wild type gene | Chemically synthesized gene |
|---|---|---|
| Size of polynucleotide (bp) | 879 | 879 |
| Gene identity (%) | 100 | 77 |
| Translated amino acid (a.a.) | 293 | 293 |
| GC content (%) | 53.23 | 44.70 |
| Stability of RNA $2^{nd}$ structure ($\Delta G°$, kcal/mol) | −423.8 | −338.4 |

TABLE 2

| Codon | Content (%) Wild type | Content (%) Synthesized type | Codon | Content (%) Wild type | Content (%) Synthesized type | Codon | Content (%) Wild type | Content (%) Synthesized type | Codon | Content (%) Wild type | Content (%) Synthesized type |
|---|---|---|---|---|---|---|---|---|---|---|---|
| TTT | 1.70 | 2.38 | TCT | 1.02 | 1.36 | TAT | 1.36 | 2.04 | TGT | 0.00 | 0.68 |
| TTC | 3.41 | 2.73 | TCC | 1.02 | 1.70 | TAC | 3.07 | 2.38 | TGC | 1.02 | 0.34 |
| TTA | 0.00 | 0.68 | TCA | 0.34 | 1.36 | TAA | 0.00 | 0.00 | TGA | 0.34 | 0.34 |

TABLE 2-continued

| Codon | Content (%) Wild type | Content (%) Synthesized type | Codon | Content (%) Wild type | Content (%) Synthesized type | Codon | Content (%) Wild type | Content (%) Synthesized type | Codon | Content (%) Wild type | Content (%) Synthesized type |
|---|---|---|---|---|---|---|---|---|---|---|---|
| TTG | 0.68 | 2.04 | TCG | 0.34 | 0.68 | TAG | 0.00 | 0.00 | TGG | 3.41 | 3.41 |
| CTT | 0.68 | 0.68 | CCT | 1.36 | 1.02 | CAT | 1.02 | 1.36 | CGT | 1.36 | 0.68 |
| CTC | 2.04 | 0.00 | CCC | 0.68 | 0.34 | CAC | 1.70 | 1.36 | CGC | 1.02 | 0.00 |
| CTA | 0.00 | 0.34 | CCA | 0.00 | 1.02 | CAA | 1.02 | 2.38 | CGA | 0.34 | 0.34 |
| CTG | 1.36 | 1.02 | CCG | 0.34 | 0.00 | CAG | 2.73 | 1.36 | CGG | 0.34 | 0.00 |
| ATT | 1.70 | 2.04 | ACT | 1.36 | 3.75 | AAT | 3.75 | 3.75 | AGT | 0.68 | 0.68 |
| ATC | 2.38 | 2.38 | ACC | 5.46 | 1.36 | AAC | 2.38 | 2.38 | AGC | 2.73 | 0.68 |
| ATA | 1.02 | 0.68 | ACA | 1.02 | 2.73 | AAA | 1.36 | 2.04 | AGA | 0.34 | 2.04 |
| ATG | 2.38 | 2.38 | ACG | 0.68 | 0.68 | AAG | 2.38 | 1.70 | AGG | 0.68 | 0.68 |
| GTT | 1.70 | 2.38 | GCT | 2.73 | 5.11 | GAT | 3.75 | 3.41 | GGT | 2.38 | 6.48 |
| GTC | 2.38 | 1.36 | GCC | 3.07 | 1.70 | GAC | 2.73 | 3.07 | GGC | 4.43 | 1.02 |
| GTA | 0.34 | 0.68 | GCA | 2.04 | 3.07 | GAA | 1.70 | 1.36 | GGA | 2.38 | 3.41 |
| GTG | 1.36 | 1.36 | GCG | 2.04 | 0.00 | GAG | 1.02 | 1.36 | GGG | 1.70 | 0.00 |

Example 2: Cloning and Construction of a Transformant Strain for the Production of the *Polyporus squamosus*-Derived Recombinant Lectin Protein from *E. coli*

Polymerase chain reaction (PCR) was performed to produce the *Polyporus squamosus*-derived recombinant lectin protein from *E. coli*.

Figure 1:
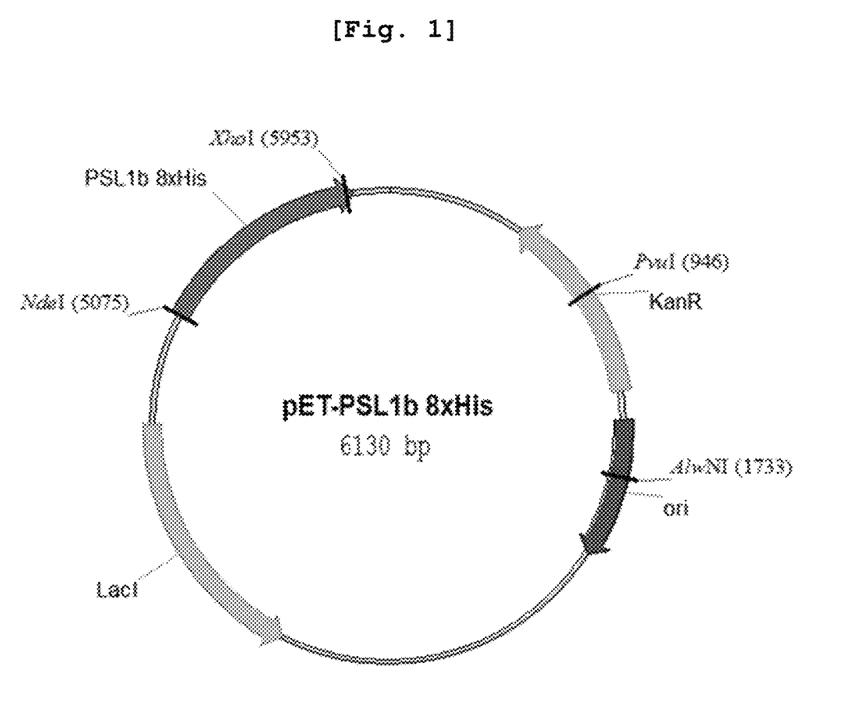
FIG. 1 is a schematic diagram illustrating the plasmid pET-PSL1b 8× His expressing the recombinant lectin PSL1b binding specifically to alpha(2,6) sialic acid originated from *Polyporus squamosus* which has been chemically synthesized in *E. coli*.

Particularly, primers were constructed for the cloning of the lectin protein of Example 1 into the *E. coli* expression vector based on the gene information of the polynucleotide identified by the method of Example 1. As shown in Table 3, the constructed primers are represented by SEQ. ID. NO: 3 and SEQ. ID. NO: 4. Polymerase chain reaction (PCR) was performed by using the chemically synthesized polynucleotide as a template. PCR conditions for the amplification of the 897 gene encoding the said lectin gene were as follows: denaturation at 94° C. for 30 seconds, annealing at 52° C. for 30 seconds, extension at 72° C. for 1 minute 20 seconds, 35 cycles from denaturation to extension. The amplified gene was purified with DNA purification kit (QIAGEN PCR purification kit, Valencia, Calif., USA). The purified gene and the vector pET39b (Novagen, USA) for the cloning of a corresponding gene in *E. coli* were treated with proper restriction enzymes and the gene fragment treated with the restriction enzymes was separated on agarose gel, followed by purification using the same purification kit as the above. The purified gene fragment was ligated with the cloning vector pET39b, and *E. coli* DH5α was transfected with the vector. Plasmid was separated from the transfected *E. coli*, followed by DNA sequencing (Genotech, Daejeon, Korea). The final recombinant plasmid prepared by the method above was named 'pET-PSL1b 8× His' (FIG. 1). The gene cloned into the expression vector was 909 bp (SEQ. ID. NO: 5) that could encode the recombinant lectin protein produced in *E. coli* and was encoding the amino acid sequence comprising total 302 amino acid residues represented by SEQ. ID. NO: 6 and had 8 histidines at C-terminal, by which the recombinant lectin protein could be easily separated through metal ion affinity chromatography (IMAC) column. The recombinant plasmid pET-PSL1b 8× His whose gene sequence had been identified was introduced in *E. coli* BL21-CodonPlus(DE3)-RIL to produce the recombinant lectin PSL1b protein. The recombinant strain *Escherichia coli* PSL1b expressing the recombinant lectin PSL1b was deposited at Korean Collection for Type Cultures (KCTC), Korea Research Institute of Bioscience and Biotechnology (KRIBB), on Nov. 1, 2013 (KCTC12507BP).

TABLE 3

| SEQ. ID. NO | Sequence |
|---|---|
| SEQ. ID. NO: 3 | 5'-TTTTTTTTCATATGAGTTTCGAGGGACATG GAATCTAC-3' |
| SEQ. ID. NO: 4 | 5'-TTAACTCGAGGAACAATCCAAAATATGCTT TATAAC-3' |

Example 3: Cloning and Construction of a Transformant Strain for the Production of the *Polyporus squamosus*-Derived Recombinant Lectin Protein from Yeast Polymerase chain reaction (PCR) was performed to produce the *Polyporus squamosus*-derived recombinant lectin protein from yeast.

Figure 2:
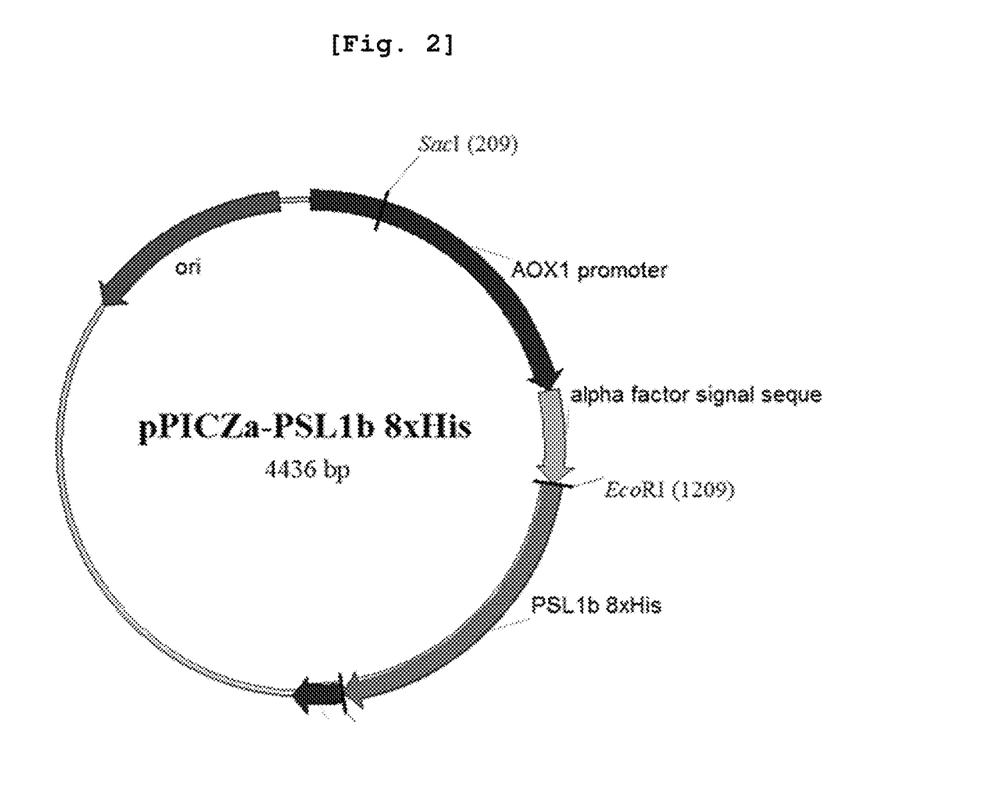
FIG. 2 is a schematic diagram illustrating the plasmid pPICZα-PSL1b 8× His expressing the recombinant lectin PSL1b binding specifically to alpha(2,6) sialic acid originated from *Polyporus squamosus* which has been chemically synthesized in yeast.

Particularly, primers were constructed for the cloning of the lectin protein of Example 1 into the yeast expression vector based on the gene information of the polynucleotide identified by the method of Example 1. As shown in Table 4, the constructed primers are represented by SEQ. ID. NO: 7 and SEQ. ID. NO: 8. Polymerase chain reaction (PCR) was performed by using the chemically synthesized polynucleotide as a template. PCR conditions for the amplification of the 915 bp gene encoding the said lectin gene were as follows: denaturation at 94° C. for 30 seconds, annealing at 52° C., for 30 seconds, extension at 72° C. for 1 minute, 40 cycles from denaturation to extension. The amplified gene was purified with DNA purification kit (QIAGEN PCR purification kit, Valencia, Calif., USA). The purified gene and the vector pPICZα (Invitrogen, Carlsbad, Calif., USA) for the cloning of a corresponding gene in yeast (*Pichia pastoris*) were treated with proper restriction enzymes and the gene fragment treated with the restriction enzymes was separated on agarose gel, followed by purification using the same purification kit as the above. The purified gene fragment was ligated with the cloning vector pPICZα, and *E. coli* DH5α was transfected with the vector. Plasmid was separated from the transfected *E. coli*, followed by DNA sequencing (Genotech, Daejeon, Korea). The final recombinant plasmid prepared by the method above was named 'pPICZα-PSL1b 8× His' (FIG. 2). The 1,173 bp long sequence (SEQ. ID. NO: 9) encoding the recombinant lectin protein produced in yeast (*Pichia pastoris*) via cloning in the expression vector above was encoding the amino acid sequence (SEQ. ID. NO: 10) comprising total 390 amino acid residues represented by SEQ. ID. NO: 8 and had signal peptide comprising 89 amino acid residues at its N-terminus regions and had 8 histidines at its C-terminus regions, by which the recombinant lectin protein could be easily separated through immobilized metal ion affinity chromatography (IMAC) column. The recombinant plasmid pPICZα-PSL1b 8× His whose gene sequence had been identified was introduced in *Pichia pastoris* X-33 to produce the recombinant lectin PSL1b protein. The recombinant strain *Pichia pastoris* PSL1b expressing the recombinant lectin PSL1b was deposited at Korean Collection for Type Cultures (KCTC), Korea Research Institute of Bioscience and Biotechnology (KRIBB), on Oct. 7, 2013 (KCTC12500BP).

TABLE 4

| SEQ. ID. NO | Sequence |
|---|---|
| Pp_PSL1b-F (SEQ. ID. NO: 7) | 5'-AGAATTCTCTTTCGAGGGACATGGAATCTAC-3' |
| Pp_PSL1b-R (SEQ. ID. NO: 8) | 5'-AATCTAGATCAGTGATGGTGATGGTGATGGTGATGGAACAACCCAAAATATGCTTTATAAC-3' |

Example 4: Purification of the Recombinant Lectin from *E. coli*

<4-1> Recombinant *E. coli* Strain Culture

The recombinant *E. coli* constructed by the method described in Example 2 was pre-cultured in Luria-Bertani (LB) medium (trypton 10 g/L, yeast extract 5 g/L, NaCl 10 g/L) containing antibiotics at 37° C. for at least 10 hours. The pre-culture solution of the recombinant *E. coli* was inoculated in LB medium at the volume of 1/100, followed by culture at 37° C. until $OD_{600}$ reached 0.6~0.8. To induce the expression of the recombinant PSL1b lectin, isopropyl-βD-thiogalactopyranoside (IPTG) was added thereto at the final concentration of 1.0 mM, followed by further culture at 30° C. for 6 hours. The cells were collected from the culture solution by centrifugation.

<4-2> Separation of the Recombinant Lectin by HisTrap™ FF Column Chromatography

To separate the recombinant lectin from the cells obtained by the method described in Example <4-1>, chromatography was performed using a HisTrap™ FF chromatography column.

Particularly, the cells obtained by the same manner as described in Example <4-1> were washed with 50 mM Tris-HCl buffer (pH 7.6) three times. The cells were then lysed by sonication for 15 minutes in the same buffer. To eliminate unbroken cells and insoluble proteins from the cell lysate, centrifugation was performed at 10,000 rpm for 30 minutes. And the resultant cell residues precipitated in there were eliminated. The cell lysate was loaded in a HisTrap™ FF column (0.7×2.5 cm) equilibrated with 50 mM Tris-HCl buffer (pH 8.0) containing 10 mM imidazole and 0.25 M NaCl using Amersham-Pharmacia FPLC system (GE-Healthcare, USA). The column was washed with the same buffer of 20 times the column volume. The recombinant lectin was eluted with imidazole gradient from 10 mM to 500 mM in 50 mM tris-HCl buffer (pH 8.0) containing 0.25 M NaCl. At this time, the flow rate was 1 ml per minute and the fraction size was 0.5 mL per fraction tube. The protein eluted from the fractions displaying the peaks was concentrated by using an Amicon®15 Ultra Centrifugal 10K filter.

<4-3> Separation of the Recombinant Protein by Superose 12 Column Chromatography To separate the recombinant protein separated by using the HisTrap™ FF chromatography column by the method described in Example <4-2> with more purity, chromatography was performed using a Superose® 12 column.

Particularly, the recombinant protein separated by the method described in Example <4-2> was loaded in Superose 12 column (1.0×30 cm) (GE-Healthcare, USA) equilibrated with 50 mM Tris-HCl buffer (pH 8.0). Protein was eluted according to the size using the same buffer (1 ml/min). The protein eluted from the fractions displaying the peaks was concentrated by using Amicon®Ultra Centrifugal filter 10K.

<4-4> Confirmation of the Recombinant Lectin Protein by SDS-PAGE

To confirm the recombinant protein separated by the method of Example <4-3> with more purity, SDS-PAGE was performed.

Particularly, the crude enzyme solution obtained by the method of Example <4-3> was separated by SDS-PAGE, followed by staining with Coommassie Brilliant Blue. The purity and size of the purified lectin protein was analyzed by using Precision Plus Protein™ Standards (Bio-Rad, USA) as the standard proteins.

Figure 3:
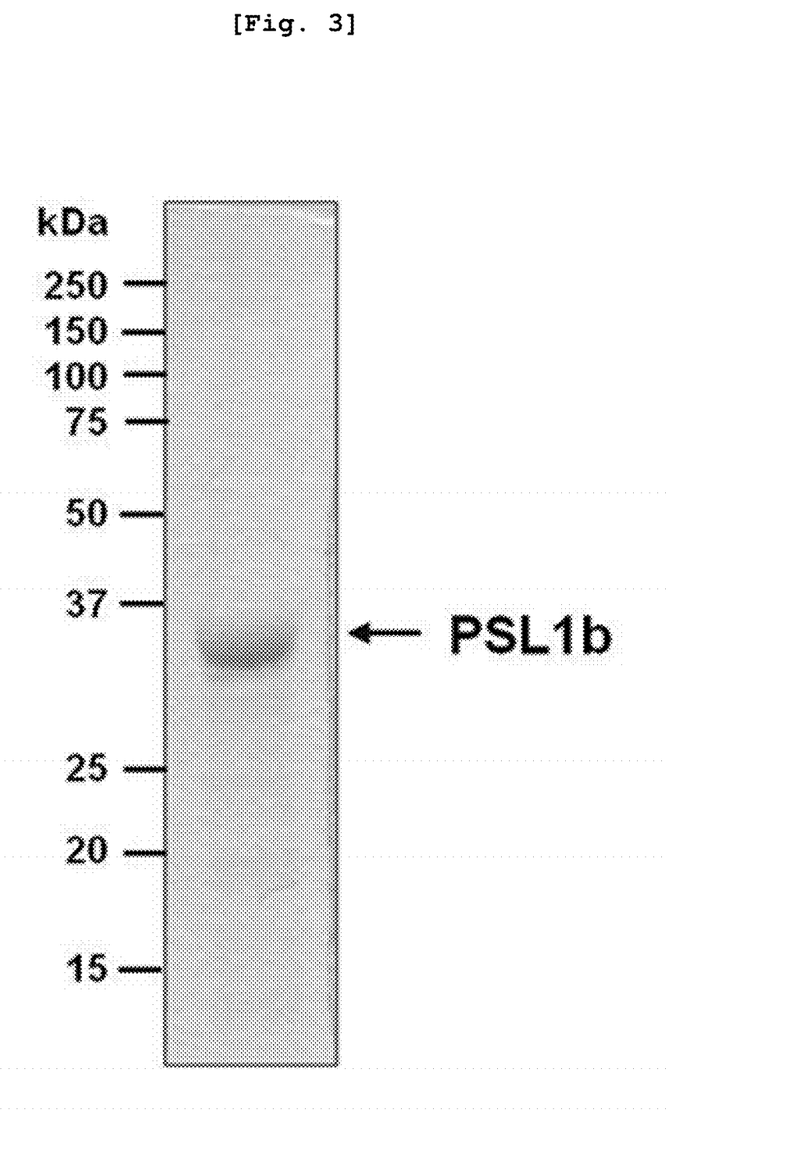
FIG. 3 is a diagram illustrating the recombinant lectin produced in *E. coli*, confirmed by SDS-PAGE.

As a result, as shown in FIG. 3, the size of the recombinant PSL1b protein separated and purified from *E. coli* was about 32 kDa (FIG. 3).

Example 5: Purification of the Recombinant Lectin from Yeast

<5-1> Recombinant Yeast Strain Culture

The recombinant yeast strain constructed by the method described in Example 3 was pre-cultured in YPD medium (Yeast extract 10 g/L, Bactopeptone 20 g/L, Dextrose 20 g/L) at 30° C. for at least 24 hours. The recombinant yeast strain pre-culture solution was inoculated in 1.5 L of main culture medium at the ratio of 1:100 (v/v). The composition of the main culture medium was as follows (per 1 liter): 50 mL glycerol, 833 mL distilled water, 0.9 g $CaSO_4$, 14.67 g $K_2SO_4$, 11.67 g $MgSO_4.7H_2O$, 9 g $(NH_4)_2SO_4$, 167 mL Hexametaphosphate solution (150 g hexametaphosphate per 1 L distilled water), and 4 mL trace element solution. Main culture was performed in 2 liter Jar fermentor (Jar fermentor, Kobiotech, Korea). The yeast was cultured at the aeration rate of 0.3 vvm, 1,000 rpm, pH 4.8~6.4, 30° C. pH was controlled during the culture with 10% (v/v) phosphoric acid solution and ammonia water. The yeast cells were cultured until the glycerol content in the culture medium reached up to 5 g/L. Then, 5 ml of methanol was fed thereto in order to induce the expression of the lectin protein. The methanol content in the medium was monitored at a regular interval. 1 g/L, the equivalent amount of methanol was added. 48 hours after the first methanol injection, the culture solution was collected.

<5-2> Separation of Yeast Cells and Medium

To separate the yeast cells and the culture medium from the yeast culture solution prepared by the method described in Example <5-1>, centrifugation was performed.

Particularly, centrifugation was performed using SUPRA 22K centrifuge (Hanil Science Inc., Korea) equipped with A1000S-4S rotor at 4° C., 7,000 rpm for 30 minutes. The precipitated yeast cells were discarded and the supernatant was obtained. The obtained supernatant was stirred, during which ammonium sulfate in the solid phase was slowly added thereto until the concentration reached 80% (saturation concentration). The supernatant added with ammonium sulfate was stirred at 4° C. for at least 12 hours. Then, centrifugation was performed at 4° C., 7,000 rpm for 1 hour. The supernatant was eliminated and the precipitate was obtained. The precipitate was dissolved in 50 mM Tris-HCl buffer (pH 8.0), which was loaded in Slide-A-Lyzer®dialysis Cassette (Thermo Scientific, Rockford, USA). The crude protein solution containing the recombinant protein was dialyzed in 5 L of the same buffer as the above. After 12 hours of dialysis, the crude protein solution was centrifuged using SUPRA 22K centrifuge (Hanil Science Inc., Korea) equipped with A500S-6N rotor at 4° C., 12,000 rpm for 30 minutes. The precipitate was eliminated and the supernatant was obtained.

<5-3> Separation of the Recombinant Lectin by HisTrap™ FF Column Chromatography

To separate the recombinant lectin from the crude protein solution obtained by the method described in Example <5-2>, the following experiment was performed.

Particularly, the crude protein solution was loaded in a HisTrap™ FF column (0.7×2.5 cm) equilibrated with 50 mM Tris-HCl buffer (pH 8.0) containing 10 mM imidazole and 0.25 M NaCl using Amersham-Pharmacia FPLC system (GE-Healthcare, USA). The column was washed with the same buffer at the volume of 20 times the volume of the solution. The recombinant lectin was eluted with imidazole gradient from 10 mM to 500 mM in 50 mM tris-HCl buffer (pH 8.0) containing 0.25 M NaCl. At this time, the elution rate was 1 ml per minute and the fraction size was 0.5 mL per fraction tube. The protein eluted from the fractions displaying the peaks was concentrated by using an Amicon®Ultra Centrifugal 10K filter.

<5-4> Confirmation of the Recombinant Lectin Protein by SDS-PAGE

To confirm the purified lectins in the fraction pools obtained by the method of Example <5-3>, SDS-PAGE was performed.

Particularly, the purified lectins in the fraction pools obtained by the method of Example <5-3> was separated by SDS-PAGE, followed by staining with Coommassie Brilliant Blue. The purity and the molecular weight of the purified lectin protein was analyzed by using Precision Plus Protein™ Standards (Bio-Rad, USA) as the standard proteins.

Figure 4:
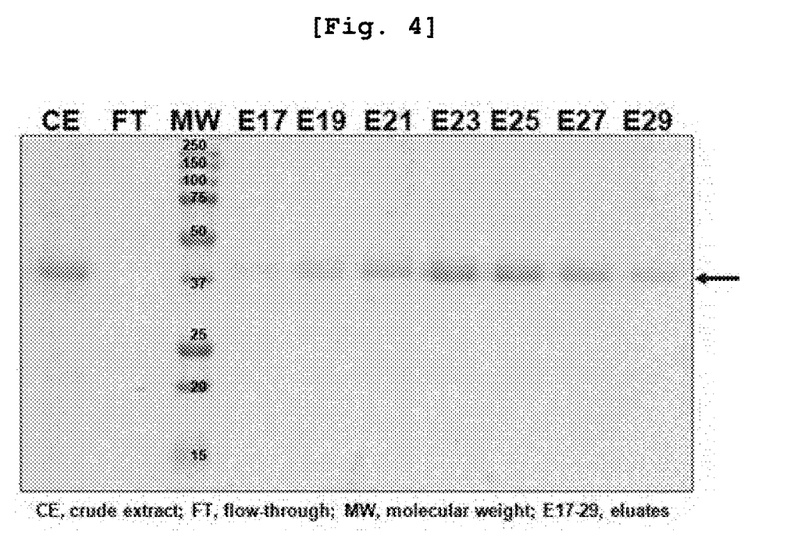
FIG. 4 is a diagram illustrating the recombinant lectin produced in yeast, confirmed by SDS-PAGE.

As a result, as shown in FIG. 4, the size of the recombinant PSL1b protein separated and purified from yeast above was about 40 kDa, which was a little bigger than the size of the recombinant PSL1b protein separated and purified from E. coli. The size difference was assumed due to the potential three N-linked glycosylation sites included in the corresponding lectin sequence.

Example 6: Measurement of Glycoprotein Containing Sialic Acid Moieties by Lectin Blot Analysis Lectin blotting was performed to investigate the selective binding force of the protein separated by the method of Example <5-4>.

Particularly, lectin blotting was performed with the glycoprotein wherein sialylation was completed by the reaction between non-sialylated glycoprotein not added with sialic acid sugar chains and CMP-N-acetylneuraminic acid (CMP-Neu5Ac) in the presence of α(2,6)-sialyltransferase. For in vitro sialylation, the cell extract expressing α(2,6)-sialyltransferase was mixed with 1 mg/mL of the sialic acid receptor non-sialylated fetuin (asialofetuin) as a glycoprotein substrate, 0.5 mg/mL of the sialic acid donor CMP-Neu5Ac, 10 mM $MnCl_2$, 1% Triton X-100, and 0.02 unit TEV (Tobacco Etch Virus) protease in PBS (phosphate buffered saline), followed by reaction at 25° C. for 6 hours. After the enzymatic sialyation, the sialylated glycoprotein was analyzed by lectin blotting to confirm the addition of sialic acid. Each enzyme reaction product respectively containing non-sialylated fetuin or sialylated fetuin was mixed with 5× Laemmli buffer, which was then heated for 10 minutes. The fetuin samples were separated by 8% SDS-PAGE electrophoresis. The proteins separated on the SDS-PAGE gel were transferred on a nitrocellulose membrane at 15 V for 1 hour by using Trans-Blot SD Semi-Dry Transfer Cell (Bio-Rad, USA). The protein-transferred membrane was washed with phosphate buffered saline (PBS) and then incubated in PBS containing 3% bovine serum albumin (BSA) for 1 hour. The membrane was washed again with PBS containing 0.5% Tween (PBST) 3 times and then loaded in 3% BSA-PBS containing 1 mg/ml of the biotin-conjugated recombinant PSL1b lectin protein prepared above, followed by culture at room temperature for 4 hours. The biotinylation conjugation of the recombinant PSL1b lectin protein was performed by using Antibody Biotinylation Kit (Genomine, Korea). After incubation of the membrane with the biotin-conjugated lectin, the membrane was washed with PBST 6 times for 10 minutes, followed by reaction with 0.2 mg/mL of horseradish peroxidase(HRP)-conjugated anti-biotin antibody (1:500, Sigma-Aldrich) for 1 hour. The membrane was washed with PBST 6 times for 10 minutes by the same manner as described above. At last, the sialylated protein was detected by ECL kit (GE Healthcare, USA).

Figure 5:
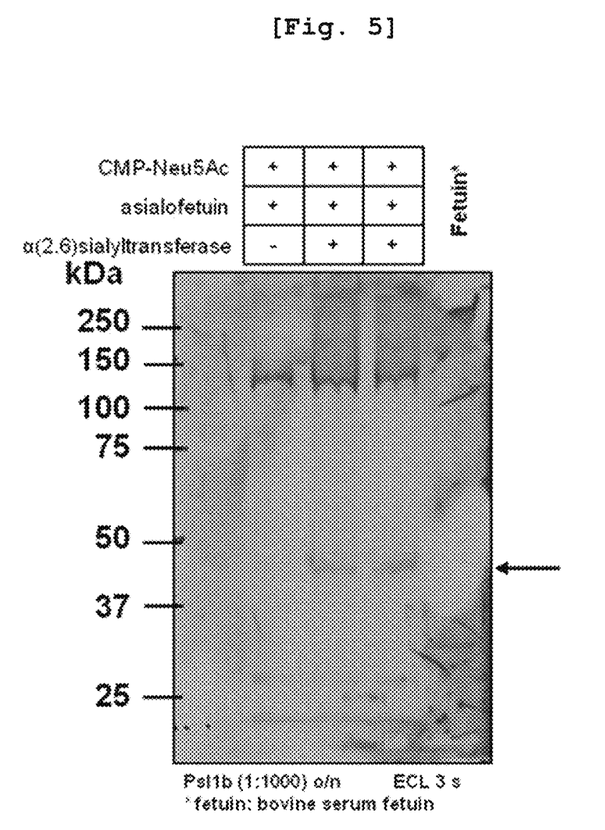
FIG. 5 is a diagram illustrating the result of lectin blotting presenting the measurement of alpha(2,6) sialic acid of the sialylated glycoprotein added with sialic acid on the asialofetuin mediated by α(2,6)-sialyltransferase by using the recombinant lectin PSL1b.

As a result, as shown in FIG. 5, lectin blot signal was observed in the basic structure of N-linked glycan such as Neu5Acα(2,6)Galβ(1,4)GlcNAc and in the fetuin containing O-linked glycans such as Neu5Acα(2,6)Galβ, Neu5Acα(2,6)Galβ(1,3)GalNA, Neu5Acα(2,6)[Galβ(1,3)]GalNA, Neu5Acα(2,6)Galβ(1,3)[Neu5Acα(2,6)]GalNAc], Neu5Acα(2,6)Galβ(1,3)[Neu5Acα(2,6)Galβ(1,4)GlcNAcβ(1,6)]GalNAc. However, any signal on the lectin blotting membrane was not observed in the non-sialylated fetuin, the negative control, which contains Galβ(1,4)GlcNAc for N-linked glycan and Galβ, Galβ(1,3)GalNA, [Galβ(1,3)]GalNA, Galβ(1,3)[Galβ(1,4)GlcNAcβ(1,6)]GalNAc for O-linked glycans, and the fetuin containing alpha(2,3) sialic acid (bovine serum fetuin) (FIG. 5).

INDUSTRIAL APPLICABILITY

The present invention relates to a method for producing, separating, and purifying the recombinant lectin as an active 
protein comprising the steps of synthesizing the polynucleotide encoding PSL1b lectin protein; and introducing the synthetic polynucleotide gene in a heterologous host to construct the recombinant strains *Escherichia coli* PSL1b (KCTC12507B) and *Pichia pastoris* PSL1b (KCTC12500BP) in order to produce the PSL1b lectin as a recombinant protein that binds specifically to alpha(2,6)-linked sialic acid. The recombinant protein of the present invention can be effectively used as an active ingredient of a composition or a kit for measuring or detecting glycoproteins, glycopeptides, glycolipids, sugar precursors, or oligosaccharides having sialic acid moieties containing the recombinant lectin specifically binding to alpha(2,6)-linked sialic acid, or a composition or a kit for measuring or detecting cell lines, bacteria, and viruses having sialoglycoconjugates containing the recombinant lectin specifically binding to alpha(2,6)-linked sialic acid.

DEPOSIT NUMBER

Depositary Authority: Korea Research Institute of Bioscience and Biotechnology
Deposit Number: KCTC12507BP
Deposit Day: 20131101
Depositary Authority: Korea Research Institute of Bioscience and Biotechnology
Deposit Number: KCTC12500BP
Deposit Day: 20131007

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preparing an active recombinant lectin of mushroom *Polyporus squamosus*-derived PSL1b binding specifically to alpha(2,6)-linked sialic acid comprising the following steps:

a) culturing a transformant transfected with an expression vector comprising a polynucleotide composed of the nucleotide sequence represented by SEQ. ID. NO: 1 encoding the lectin binding specifically to alpha(2,6)-linked sialic acid; and b) separating and purifying the active recombinant lectin binding specifically to alpha(2,6)-linked sialic acid from the culture product of step (a).

2. The method according to claim 1, wherein the transformant is a bacteria or a yeast.

3. The method according to claim 2, wherein the bacteria are selected from the group consisting of *Staphylococcus aureus, E. coli, B. cereus, Salmonella typimurium, Salmonella choleraesuis, Yersinia enterocolitica*, and *Listeria monocytogenes*.

4. The method according to claim 2, wherein the yeast is selected from the group consisting of *Pichia, Saccharomyces, Kluyveromyces, Yallowia, Hansenula*, and *Candida*.

5. The method according to claim 1, wherein the transformant is cultured in a solution containing isopropyl-βD-thiogalactopyranoside (IPTG).

* * * * *

SEQUENCE LISTING

<160> NUMBER OF SEQ ID NOS: 10

<210> SEQ ID NO 1
<211> LENGTH: 879
<212> TYPE: DNA
<213> ORGANISM: Artificial
<220> FEATURE:
<223> OTHER INFORMATION: synthesis sequence

<400> SEQUENCE: 1
atgtctttcg agggacatgg aatctaccat atccctcatg cccacgtagc taacatccga 60
atggctttag caaatagggg ctctggtcag aatggaactc cagtgattgc ttgggactcc 120
aataatgatg cctttgatca catgtggctg gtcgagccca caggagaagc agatacttac 180
acaatacaca acgtttcaac tggtacttat atggacgtca ctgctagcgc tgttgctgat 240
aacacaccaa ttatcggtta tcaaaggacc ggtaacgata accaaaagtg gattatctcg 300
caggttcaaa ctgacggtgg tgatcgtcct tggaagattc agtgcaaagc tacaggcact 360
tttgccacgc tgtactccgg tggtggtagc ggaacagcta ttgttggatg gagacttgtg 420
aatagtaacg gtaatcaaga ctgggttttc caaaaattgt cacaaacttc tgttaatgtg 480
cacgctacat tacttgcatg tggagcaact gttggtcaag actttaagaa ttacctgtac 540
gacggtttgt acctagtctt gccaagagat agaatcagtg ctatatggaa ggcatcaggt 600
ttgggagaga ctgctagacg tgatggtatc tacgattccg acgaatttgc tatgaccttc 660
aaatctgccg ctgcaacttg gggtaaggaa aatttcaaag ctgacggatt cgccattttg 720
tgtggtatga tgttcggtac gaaagcatcc accaatagac atgcatataa ctgggtggtc 780
gagagaggat cgttttccac agtaacattt ttcgaacctc agaatggtac ctattcagat 840
gacgcttggg gttataaagc atattttggc ttgttctga 879

<210> SEQ ID NO 2
<211> LENGTH: 292
<212> TYPE: PRT
<213> ORGANISM: Artificial
<220> FEATURE:
<223> OTHER INFORMATION: polypeptide

<400> SEQUENCE: 2

```
Met Ser Phe Glu Gly His Gly Ile Tyr His Ile Pro His Ala His Val
 1               5                  10                  15

Ala Asn Ile Arg Met Ala Leu Ala Asn Arg Gly Ser Gly Gln Asn Gly
            20                  25                  30

Thr Pro Val Ile Ala Trp Asp Ser Asn Asn Asp Ala Phe Asp His Met
            35                  40                  45

Trp Leu Val Glu Pro Thr Gly Glu Ala Asp Tyr Thr Ile His Asn
 50                  55                  60

Val Ser Thr Gly Thr Tyr Met Asp Val Thr Ala Ser Ala Val Ala Asp
 65                  70                  75                  80

Asn Thr Pro Ile Ile Gly Tyr Gln Arg Thr Gly Asn Asp Asn Gln Lys
                85                  90                  95

Trp Ile Ile Ser Gln Val Gln Thr Asp Gly Gly Asp Arg Pro Trp Lys
                100                 105                 110

Ile Gln Cys Lys Ala Thr Gly Thr Phe Ala Thr Leu Tyr Ser Gly Gly
                115                 120                 125

Gly Ser Gly Thr Ala Ile Val Gly Trp Arg Leu Val Asn Ser Asn Gly
            130                 135                 140

Asn Gln Asp Trp Val Phe Gln Lys Leu Ser Gln Thr Ser Val Asn Val
145                 150                 155                 160

His Ala Thr Leu Leu Ala Cys Gly Ala Thr Val Gly Gln Asp Phe Lys
                165                 170                 175

Asn Tyr Leu Tyr Asp Gly Leu Tyr Leu Val Leu Pro Arg Asp Arg Ile
                180                 185                 190

Ser Ala Ile Trp Lys Ala Ser Gly Leu Gly Glu Thr Ala Arg Arg Asp
                195                 200                 205

Gly Ile Tyr Asp Ser Asp Glu Phe Ala Met Thr Phe Lys Ser Ala Ala
                210                 215                 220

Ala Thr Trp Gly Lys Glu Asn Phe Lys Ala Asp Gly Phe Ala Ile Leu
225                 230                 235                 240

Cys Gly Met Met Phe Gly Thr Lys Ala Ser Thr Asn Arg His Ala Tyr
                245                 250                 255

Asn Trp Val Val Glu Arg Gly Ser Phe Ser Thr Val Thr Phe Phe Glu
                260                 265                 270

Pro Gln Asn Gly Thr Tyr Ser Asp Asp Ala Trp Gly Tyr Lys Ala Tyr
                275                 280                 285

Phe Gly Leu Phe
                290

<210> SEQ ID NO 3
<211> LENGTH: 38
<212> TYPE: DNA
<213> ORGANISM: Artificial
<220> FEATURE:
<223> OTHER INFORMATION: primer

<400> SEQUENCE: 3 tttttttttca tatgagtttc gagggacatg gaatctac                              38

<210> SEQ ID NO 4
<211> LENGTH: 36
<212> TYPE: DNA
<213> ORGANISM: Artificial
<220> FEATURE:
<223> OTHER INFORMATION: primer2

<400> SEQUENCE: 4
```

```
ttaactcgag gaacaatcca aaatatgctt tataac                              36
```

<210> SEQ ID NO 5
<211> LENGTH: 909
<212> TYPE: DNA
<213> ORGANISM: Artificial
<220> FEATURE:
<223> OTHER INFORMATION: lectin

<400> SEQUENCE: 5

```
atgagtttcg agggacatgg aatctaccat atccctcatg cccacgtagc taacatccga    60
atggctttag caaatagggg ctctggtcag aatggaactc cagtgattgc ttgggactcc   120
aataatgatg cctttgatca catgtggctg gtcgagccca caggagaagc agatacttac   180
acaatacaca acgtttcaac tggtacttat atggacgtca ctgctagcgc tgttgctgat   240
aacacaccaa ttatcggtta tcaaaggacc ggtaacgata ccaaaagtg gattatctcg    300
caggttcaaa ctgacggtgg tgatcgtcct tggaagattc agtgcaaagc tacaggcact   360
tttgccacgc tgtactccgg tggtggtagc ggaacagcta ttgttggatg gagacttgtg   420
aatagtaacg gtaatcaaga ctgggttttc caaaaattgt cacaaacttc tgttaatgtg   480
cacgctacat tacttgcatg tggagcaact gttggtcaag actttaagaa ttacctgtac   540
gacggtttgt acctagtctt gccaagagat agaatcagtg ctatatggaa ggcatcaggt   600
ttgggagaga ctgctagacg tgatggtatc tacgattccg acgaatttgc tatgaccttc   660
aaatctgccg ctgcaacttg gggtaaggaa aatttcaaag ctgacggatt cgccattttg   720
tgtggtatga tgttcggtac gaaagcatcc accaatagac atgcatataa ctgggtggtc   780
gagagaggat cgttttccac agtaacattt ttcgaacctc agaatggtac ctattcagat   840
gacgcttggg gttataaagc atattttgga ttgttcctcg agcaccacca ccaccaccac   900
caccactaa                                                          909
```

<210> SEQ ID NO 6
<211> LENGTH: 302
<212> TYPE: PRT
<213> ORGANISM: Artificial
<220> FEATURE:
<223> OTHER INFORMATION: polypeptide

<400> SEQUENCE: 6

```
Met Ser Phe Glu Gly His Gly Ile Tyr His Ile Pro His Ala His Val
 1               5                  10                  15

Ala Asn Ile Arg Met Ala Leu Ala Asn Arg Gly Ser Gly Gln Asn Gly
            20                  25                  30

Thr Pro Val Ile Ala Trp Asp Ser Asn Asn Asp Ala Phe Asp His Met
        35                  40                  45

Trp Leu Val Glu Pro Thr Gly Glu Ala Asp Thr Tyr Thr Ile His Asn
    50                  55                  60

Val Ser Thr Gly Thr Tyr Met Asp Val Thr Ala Ser Ala Val Ala Asp
65                  70                  75                  80

Asn Thr Pro Ile Ile Gly Tyr Gln Arg Thr Gly Asn Asp Asn Gln Lys
                85                  90                  95

Trp Ile Ile Ser Gln Val Gln Thr Asp Gly Gly Asp Arg Pro Trp Lys
            100                 105                 110

Ile Gln Cys Lys Ala Thr Gly Thr Phe Ala Thr Leu Tyr Ser Gly Gly
        115                 120                 125

Gly Ser Gly Thr Ala Ile Val Gly Trp Arg Leu Val Asn Ser Asn Gly
```

|     |     |     |     |     |     |     | 130 |     |     |     | 135 |     |     |     | 140 |     |     |

Asn Gln Asp Trp Val Phe Gln Lys Leu Ser Gln Thr Ser Val Asn Val
145                 150                 155                 160

His Ala Thr Leu Leu Ala Cys Gly Ala Thr Val Gly Gln Asp Phe Lys
                165                 170                 175

Asn Tyr Leu Tyr Asp Gly Leu Tyr Leu Val Leu Pro Arg Asp Arg Ile
                180                 185                 190

Ser Ala Ile Trp Lys Ala Ser Gly Leu Gly Glu Thr Ala Arg Arg Asp
                195                 200                 205

Gly Ile Tyr Asp Ser Asp Glu Phe Ala Met Thr Phe Lys Ser Ala Ala
                210                 215                 220

Ala Thr Trp Gly Lys Glu Asn Phe Lys Ala Asp Gly Phe Ala Ile Leu
225                 230                 235                 240

Cys Gly Met Met Phe Gly Thr Lys Ala Ser Thr Asn Arg His Ala Tyr
                245                 250                 255

Asn Trp Val Val Glu Arg Gly Ser Phe Ser Thr Val Thr Phe Phe Glu
                260                 265                 270

Pro Gln Asn Gly Thr Tyr Ser Asp Asp Ala Trp Gly Tyr Lys Ala Tyr
                275                 280                 285

Phe Gly Leu Phe Leu Glu His His His His His His
                290                 295                 300

<210> SEQ ID NO 7
<211> LENGTH: 31
<212> TYPE: DNA
<213> ORGANISM: Artificial
<220> FEATURE:
<223> OTHER INFORMATION: primer

<400> SEQUENCE: 7
agaattctct ttcgagggac atggaatcta c                            31

<210> SEQ ID NO 8
<211> LENGTH: 61
<212> TYPE: DNA
<213> ORGANISM: Artificial
<220> FEATURE:
<223> OTHER INFORMATION: primer2

<400> SEQUENCE: 8
aatctagatc agtgatggtg atggtgatgg tgatggaaca acccaaaata tgctttataa    60
c                                                                   61

<210> SEQ ID NO 9
<211> LENGTH: 1173
<212> TYPE: DNA
<213> ORGANISM: Artificial
<220> FEATURE:
<223> OTHER INFORMATION: lectin

<400> SEQUENCE: 9
atgagatttc cttcaatttt tactgctgtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaagggta    240 tctctctcga gaaaagagagc tgaagctgaa ttctctttcg agggacatgg aatctaccat   300
atccctcatg cccacgtagc taacatccga atggctttag caaatagggg ctctggtcag   360

```
aatgaactc cagtgattgc ttgggactcc aataatgatg cctttgatca catgtggctg    420
gtcgagccca caggagaagc agatacttac acaatacaca acgtttcaac tggtacttat    480
atggacgtca ctgctagcgc tgttgctgat aacacaccaa ttatcggtta tcaaaggacc    540
ggtaacgata accaaaagtg gattatccgt caggttcaaa ctgacggtgg tgatcgtcct    600
tggaagattc agtgcaaagc tacaggcact tttgccacgc tgtactccgg tggtggtagc    660
ggaacagcta ttgttggatg gagacttgtg aatagtaacg gtaatcaaga ctgggttttc    720
caaaaattgt cacaaacttc tgttaatgtg cacgctacat tacttgcatg tggagcaact    780
gttggtcaag actttaagaa ttacctgtac gacggtttgt acctagtctt gccaagagat    840
agaatcagtg ctatatggaa ggcatcaggt ttgggagaga ctgctagacg tgatggtatc    900
tacgattccg acgaatttgc tatgaccttc aaatctgccg ctgcaacttg ggtaaggaa     960 aatttcaaag ctgacggatt cgccatttg tgtggtatga tgttcggtac gaaagcatcc    1020
accaatagac atgcatataa ctgggtggtc gagagaggat cgttttccac agtaacattt    1080
ttcgaacctc agaatggtac ctattcagat gacgcttggg gttataaagc atattttggc    1140
ttgttccatc accatcacca tcaccatcac tga                                 1173
```

<210> SEQ ID NO 10
<211> LENGTH: 390
<212> TYPE: PRT
<213> ORGANISM: Artificial
<220> FEATURE:
<223> OTHER INFORMATION: polypeptide sequence

<400> SEQUENCE: 10

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Ser Phe Glu Gly His
                85                  90                  95

Gly Ile Tyr His Ile Pro His Ala His Val Ala Asn Ile Arg Met Ala
            100                 105                 110

Leu Ala Asn Arg Gly Ser Gly Gln Asn Gly Thr Pro Val Ile Ala Trp
        115                 120                 125

Asp Ser Asn Asn Asp Ala Phe Asp His Met Trp Leu Val Glu Pro Thr
    130                 135                 140

Gly Glu Ala Asp Thr Tyr Thr Ile His Asn Val Ser Thr Gly Thr Tyr
145                 150                 155                 160

Met Asp Val Thr Ala Ser Ala Val Ala Asp Asn Thr Pro Ile Ile Gly
                165                 170                 175

Tyr Gln Arg Thr Gly Asn Asp Asn Gln Lys Trp Ile Ile Arg Gln Val
            180                 185                 190

Gln Thr Asp Gly Gly Asp Arg Pro Trp Lys Ile Gln Cys Lys Ala Thr
        195                 200                 205

Gly Thr Phe Ala Thr Leu Tyr Ser Gly Gly Gly Ser Gly Thr Ala Ile
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 210 |     |     |     | 215 |     |     |     | 220 |     |     |     |
| Val | Gly | Trp | Arg | Leu | Val | Asn | Ser | Asn | Gly | Asn | Gln | Asp | Trp | Val | Phe |
| 225 |     |     |     | 230 |     |     |     | 235 |     |     |     |     |     | 240 |
| Gln | Lys | Leu | Ser | Gln | Thr | Ser | Val | Asn | Val | His | Ala | Thr | Leu | Leu | Ala |
|     |     |     | 245 |     |     |     |     | 250 |     |     |     |     | 255 |     |
| Cys | Gly | Ala | Thr | Val | Gly | Gln | Asp | Phe | Lys | Asn | Tyr | Leu | Tyr | Asp | Gly |
|     |     |     | 260 |     |     |     |     | 265 |     |     |     |     | 270 |     |
| Leu | Tyr | Leu | Val | Leu | Pro | Arg | Asp | Arg | Ile | Ser | Ala | Ile | Trp | Lys | Ala |
|     |     | 275 |     |     |     |     | 280 |     |     |     |     | 285 |     |     |
| Ser | Gly | Leu | Gly | Glu | Thr | Ala | Arg | Arg | Asp | Gly | Ile | Tyr | Asp | Ser | Asp |
|     | 290 |     |     |     |     | 295 |     |     |     |     | 300 |     |     |     |
| Glu | Phe | Ala | Met | Thr | Phe | Lys | Ser | Ala | Ala | Ala | Thr | Trp | Gly | Lys | Glu |
| 305 |     |     |     |     | 310 |     |     |     |     | 315 |     |     |     |     | 320 |
| Asn | Phe | Lys | Ala | Asp | Gly | Phe | Ala | Ile | Leu | Cys | Gly | Met | Met | Phe | Gly |
|     |     |     |     | 325 |     |     |     |     | 330 |     |     |     |     | 335 |     |
| Thr | Lys | Ala | Ser | Thr | Asn | Arg | His | Ala | Tyr | Asn | Trp | Val | Val | Glu | Arg |
|     |     |     |     | 340 |     |     |     | 345 |     |     |     |     | 350 |     |     |
| Gly | Ser | Phe | Ser | Thr | Val | Thr | Phe | Phe | Glu | Pro | Gln | Asn | Gly | Thr | Tyr |
|     |     | 355 |     |     |     |     |     | 360 |     |     |     | 365 |     |     |     |
| Ser | Asp | Asp | Ala | Trp | Gly | Tyr | Lys | Ala | Tyr | Phe | Gly | Leu | Phe | His | His |
|     |     | 370 |     |     |     |     | 375 |     |     |     |     | 380 |     |     |     |
| His | His | His | His | His | His |     |     |     |     |     |     |     |     |     |     |
| 385 |     |     |     |     | 390 |     |     |     |     |     |     |     |     |     |     |